United States Patent [19]
Schmid

[11] Patent Number: 5,159,927
[45] Date of Patent: Nov. 3, 1992

[54] VISUAL PROSTHESIS APPARATUS AND METHOD

[76] Inventor: Ferdinand Schmid, 1205 Maple St., Santa Monica, Calif. 90405

[21] Appl. No.: 681,101

[22] Filed: Apr. 5, 1991

Related U.S. Application Data

[63] Continuation-in-part of Ser. No. 385,269, Jul. 26, 1989, abandoned.

[51] Int. Cl.⁵ ............................................. A61N 1/00
[52] U.S. Cl. ................................... 128/419 R; 623/4; 358/94
[58] Field of Search ...................... 623/4; 128/419 R; 358/94, 209

[56] References Cited

U.S. PATENT DOCUMENTS

| | | | |
|---|---|---|---|
| 2,721,316 | 10/1955 | Shaw | 128/419 R |
| 3,628,193 | 12/1971 | Collins | 128/419 R |
| 4,611,596 | 9/1986 | Wasserman | 128/419 R |
| 4,628,933 | 12/1986 | Michelson | 128/419 R |
| 4,837,049 | 6/1989 | Byers et al. | 128/784 |
| 4,979,508 | 12/1990 | Beck | 128/419 R |
| 5,016,633 | 5/1991 | Chow | 128/419 R |

FOREIGN PATENT DOCUMENTS

| | | | |
|---|---|---|---|
| 0171166 | 2/1986 | European Pat. Off. | 128/419 R |
| 2016378 | 11/1971 | Fed. Rep. of Germany | 623/4 |
| 2016276 | 9/1979 | United Kingdom | 128/419 R |

OTHER PUBLICATIONS

"Using Electronics to Help Blind," Electronics, Dec. 1957, p. 24.
"Artificial Vision: A Big Step Forward," Science News, Feb. 1975, vol. 105, No. 5, p. 105.
"Blind Men 'See' the Light," Washington Star News, Feb. 12, 1974, pp. A-1 & A-6.

Primary Examiner—William E. Kamm
Assistant Examiner—Kennedy J. Schaetzle
Attorney, Agent, or Firm—Robert J. Schaap

[57] ABSTRACT

A visual prosthesis apparatus for operative insertion in the optical pathway to the brain of an individual who has an eye which is blind or partially blind. The prosthesis apparatus utilizes a video camera capable of generating video signals in response to the viewing of an image. The apparatus also includes a prosthesis device or so-called insert for insertion in the eye socket in place of the diseased or damaged eye. A cable is provided for electrically connecting the output of a video camera to the insert and for delivering video signals over individual conductors in this cable to the insert. An optical nerve connecting assembly is located in the insert and has terminals for connections to the individual conductors of the cable and to the optical nerves. In this way, there is an electrical connection between each conductor and an optical nerve through the nerve connecting assembly for delivering the individual video signals to the brain. A method of using this prosthesis is also disclosed.

19 Claims, 5 Drawing Sheets

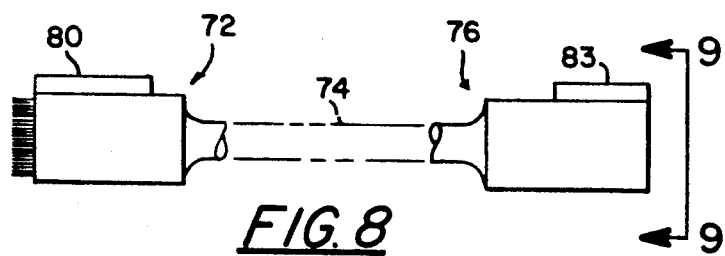 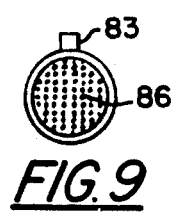
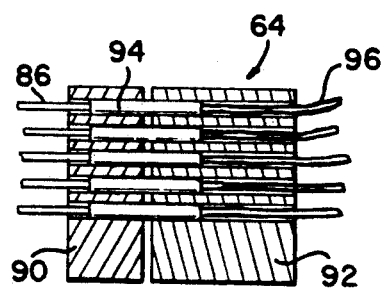
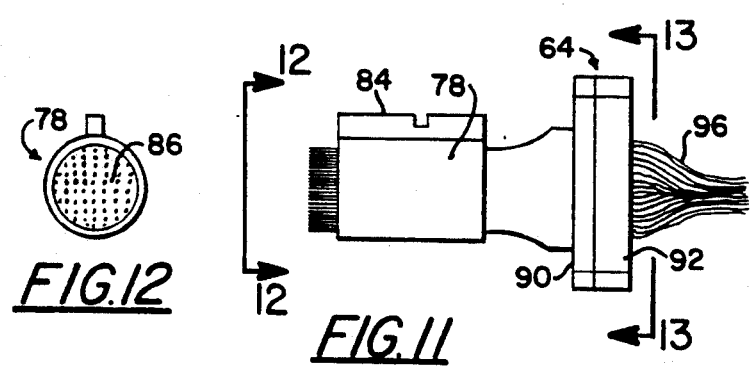 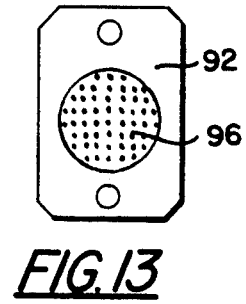
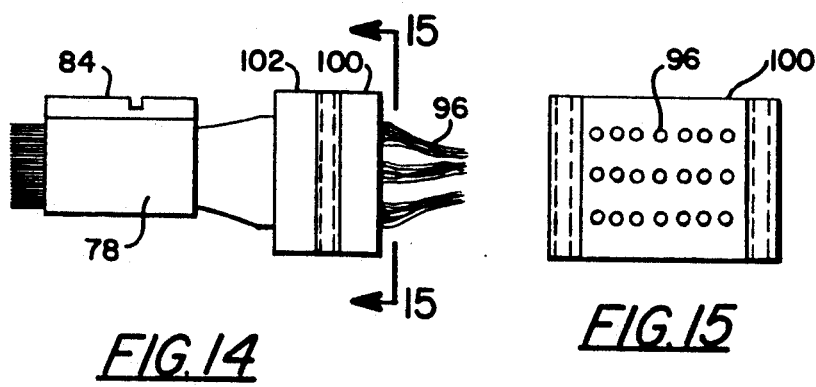

VISUAL PROSTHESIS APPARATUS AND METHOD

RELATED APPLICATION

This application is a continuation-in-part patent application of my co-pending application Ser. No. 385,269 filed Jul. 25, 1989 for "Video Electronic Eye" now abandoned.

BACKGROUND OF THE INVENTION

1. Field of the Invention

This invention relates in general to certain new and useful improvements in video prosthesis apparatus and more particularly, to a video prosthesis apparatus and a method of use therefore which is capable of being inserted in the optical pathway to the brain of an individual and which utilizes video signals of an image for transmission through the optical nerves to the brain.

2. Brief Description of the Prior Art

Recent advances in medical sciences, and particularly in opthomologic sciences, has enabled physicians to correct many eye deficiencies including cataracts and other opaqueness in the eye. However, there are many causes of blindness which are not associated with the optic nerves, but rather with the eye itself. Very often, these causes of blindness involves an obstruction or growth in the optical pathway in the eye. Furthermore, cataracts and complications arising from treatment of cataracts have also interfered with the visual process.

Many of the diseases which affect vision typically affect the eye itself but leave the optical pathway and particularly the optical nerves in-tact. Thus, if some means were provided for using a prosthesis in place of an eye for transmitting images to the brain, at least some of the visual process could be restored. It is recognized that the optical nerves have approximately one million nerve fibers. However, in actual practice, there are only approximately 50 optical nerves. While the optical fibers are clearly important in transmitting visual images, each nerve essentially carries a single message of a visual image and that visual image composite is re-generated in the brain of an individual at the cortex. Thus, while many in the field of optical vision have thought that the use of a prosthesis would have little or no benefit, the contrary is found in that the use of present day video technology enables the generation of electrical signals representing a visual image much in the same manner as an electrical signal is generated for transmission to the brain in response to an image.

The fact that there are only about fifty optical nerves for transmission of signals representing an image to the cortex of the brain suggests that there is a reasonable likelihood of development of a prosthesis which could be used in place of a diseased or damaged eye.

There have been some attempts to develop visual and/or auditory prosthesis devices. Exemplary of these attempts are U.S. Pat. No. 4,611,596 to Wasserman. This patent provides a method for utilizing a prosthesis which uses sensory codes for simulating a natural sensory code to recognize and identify a signal on an associated receptor. U.S. Pat. No. 4,628,933 to Michelson discloses a visual prosthesis device for overcoming the problems of retinal malfunction. U.S. Pat. No. 4,628,933 to Michelson also teaches of the use of a plurality of electrodes which are adapted to be inserted in the posterior chamber of the eye. The electrodes are operatively connected to a neuron array at the surface of the retina.

Heretofore, U.S. Pat. No. 3,628,193 to Collins discloses a tactile image projection system which can be used with a blind individual and British Patent No. 2,016,276 discloses a system which uses a prosthesis for stimulating the brain.

OBJECTS OF THE INVENTION

It is, therefore, one of the primary objects of the present invention to provide a prosthesis apparatus which utilizes synthetically created signals transmitted through the optical nerve system of a person having a blind or partially blind eye to recreate a representation of the image in the brain of such individual.

It is another object of the present invention to provide a prosthesis apparatus of the type stated in which an eye prothesis is inserted into the eye cavity in place of the diseased or injured eye.

It is a further object of the present invention to provide an eye prothesis apparatus of the type stated which provides for a connection to each of the optical nerves for transmitting electrical signals to the brain to thereby re-create a representation of an observed image.

It is an additional object of the present invention to provide a method for aiding visual activity in a person having a diseased or injured eye which is blind or partially blind utilizing the video signals for transmission through the optical nerve system to the brain of an individual.

It is still another object of the present invention to provide a prosthesis apparatus of the type stated and a method which is highly effective in use and which can be employed at a relatively low cost.

With the above and other objects in view, my invention resides in the novel features of form, construction, arrangement and combination of parts presently described and pointed out in the claims.

BRIEF SUMMARY OF THE INVENTION

The present invention relates in general terms to an eye prosthesis apparatus which utilizes a video camera attached to the individual using the eye prosthesis apparatus. This apparatus is highly effective for aiding and replenishing of vision to a person having a blind or partially blind eye and in which the optical nerve system remains in-tact and operable. The prothesis apparatus of the invention employs a video camera, as aforesaid. When scanning an image, this video camera generate signals representative of that image.

A prothesis device is inserted into the eye cavity in place of a diseased or injured eye. In this case, the diseased or injured eye would necessarily be severed and removed from the optical nerve. It has been found in actual practice that there are only approximately fifty optical nerves. Thus, a separation of the eye from the optical nerve bundle does not create a significant problem.

The output of the video camera is connected to a connector assembly located in the eye prosthesis device introduced into the eye cavity. This connector assembly includes a plurality of connector pins, one for each of the optical nerves, and these pins are thereupon connected to the individual ones of the optical nerves. In this way, each optical nerve receives a different electrical signal from the video camera and where all of the electrical signals represents the scanned image.

When the electrical signals are introduced into the brain, there is a re-creation of the image observed by the video camera. It is necessary to determine which optical nerve can be connected to which electrical conductor in order to simulate the actual vision process. In this case, a computerized process in which each optical nerve is connected to an individual electrical conductor is employed. When the user of the prothesis apparatus detects a spot of light from connecting of an optical nerve to an individual conductor, that combination is noted. When all combinations produce a spot of light, then a proper electrical pattern has been created.

The present invention also provides an electrical circuit which is useful with the eye prothesis apparatus and which enables the simulation of sight by recreation of an image observed by the video camera.

This invention possesses many other advantages and has other objects and advantages which will become more clearly apparent from a consideration of the forms in which it may be embodied. The following detailed description illustrates one practical embodiment of the invention, although it is to be understood that this detailed description is set forth only for the purpose of illustrating the principles of the invention, but it is to be understood that such detailed description is not to be taken in a limiting sense.

BRIEF DESCRIPTION OF THE DRAWINGS

Figure 1:
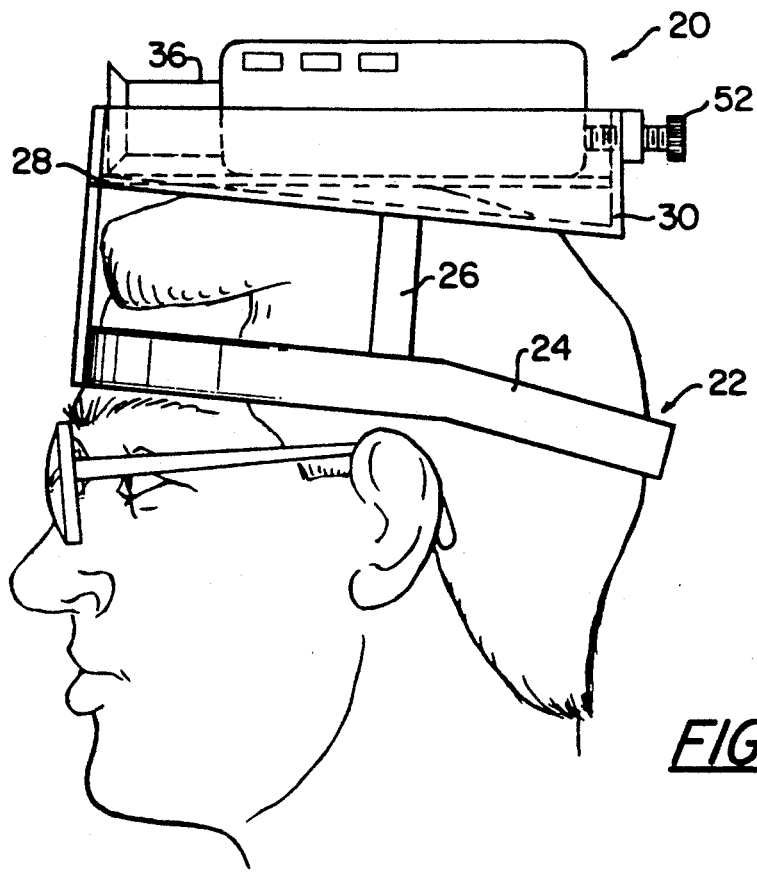
Figure 2:
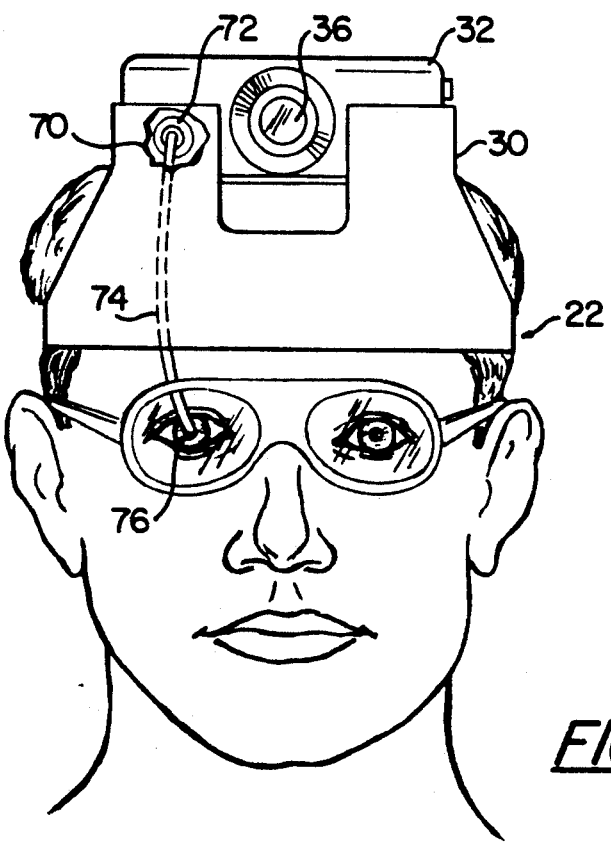
Figure 3:
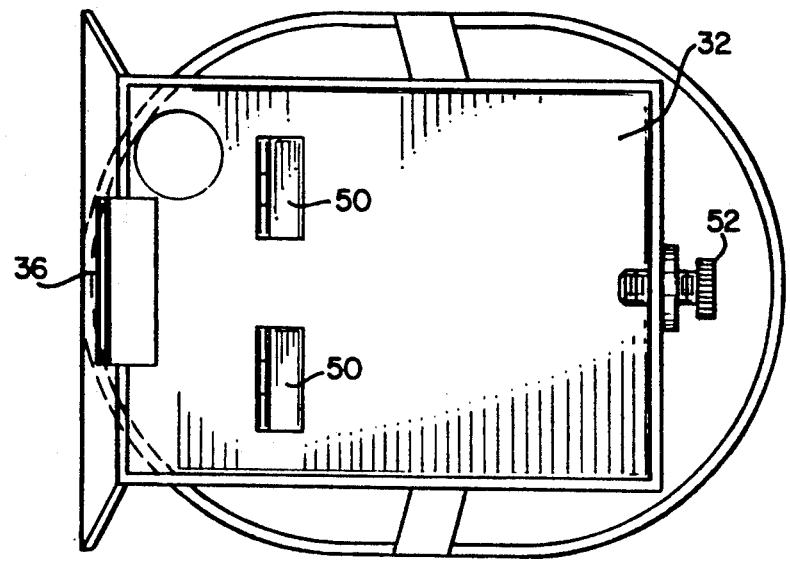
Figure 4:
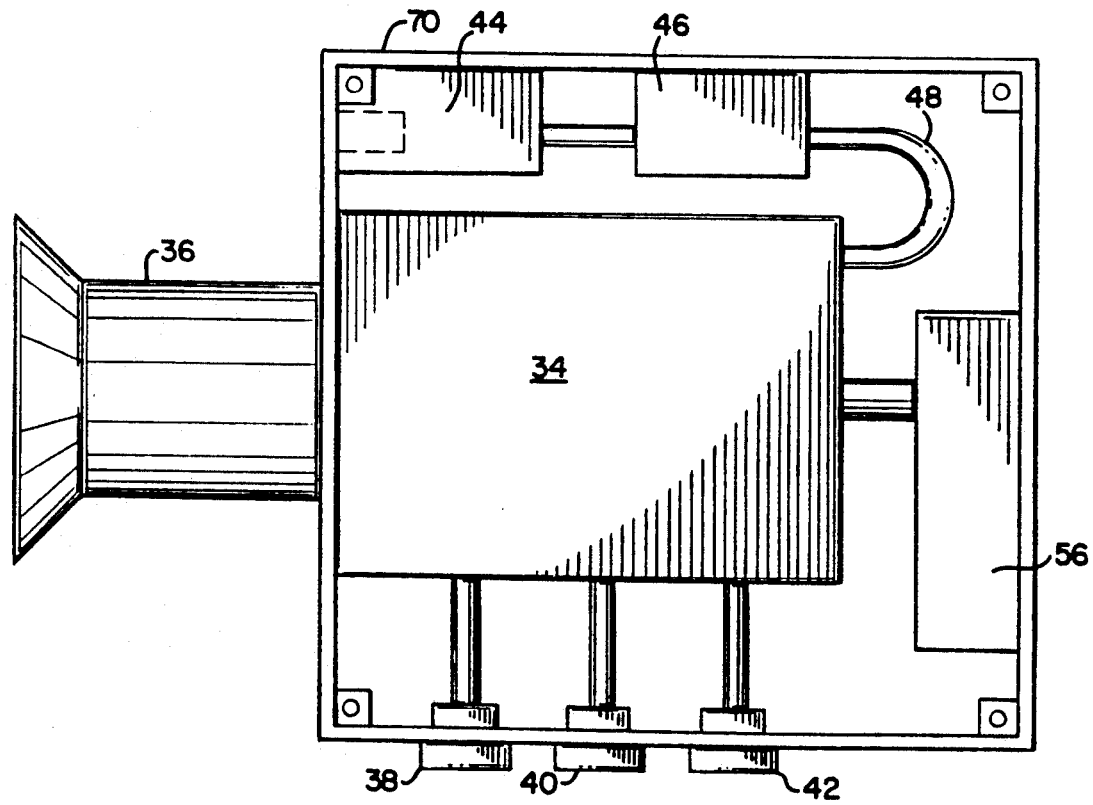
Figure 5:
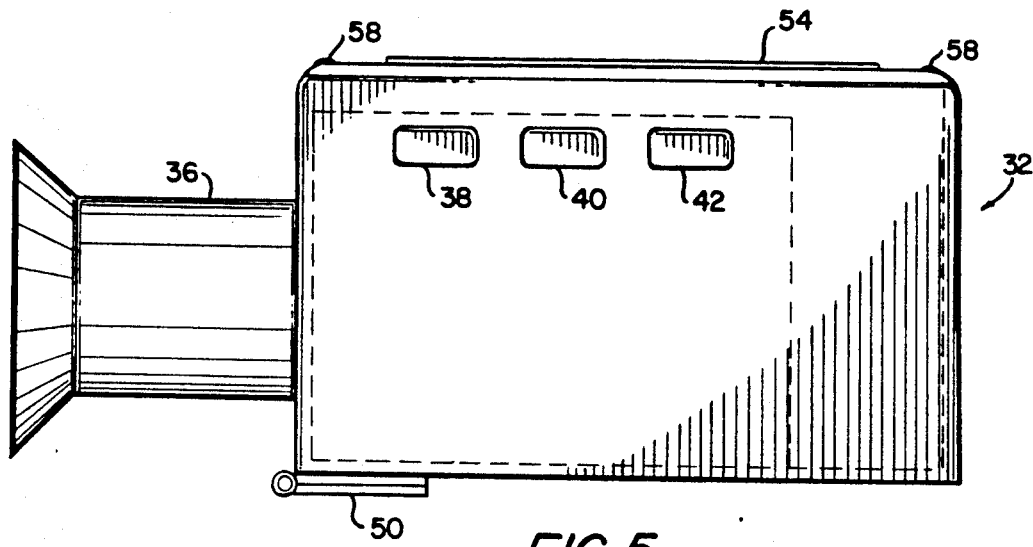
Figure 6:
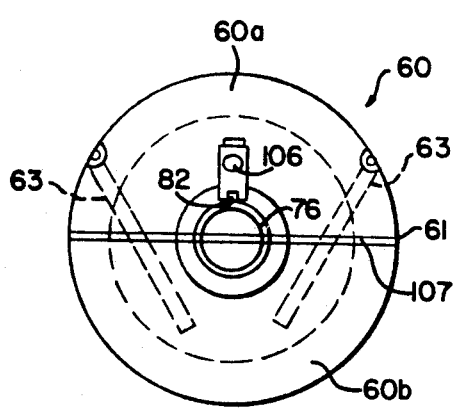
Figure 7:
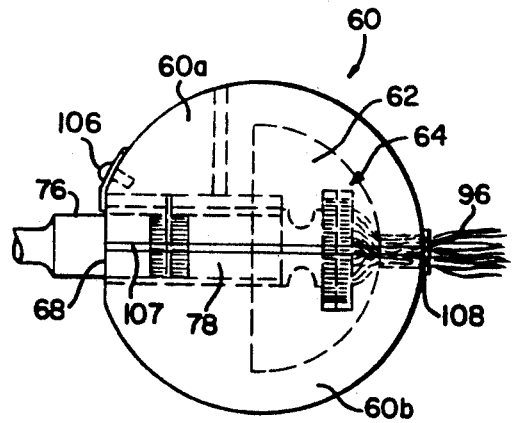
Figure 16:
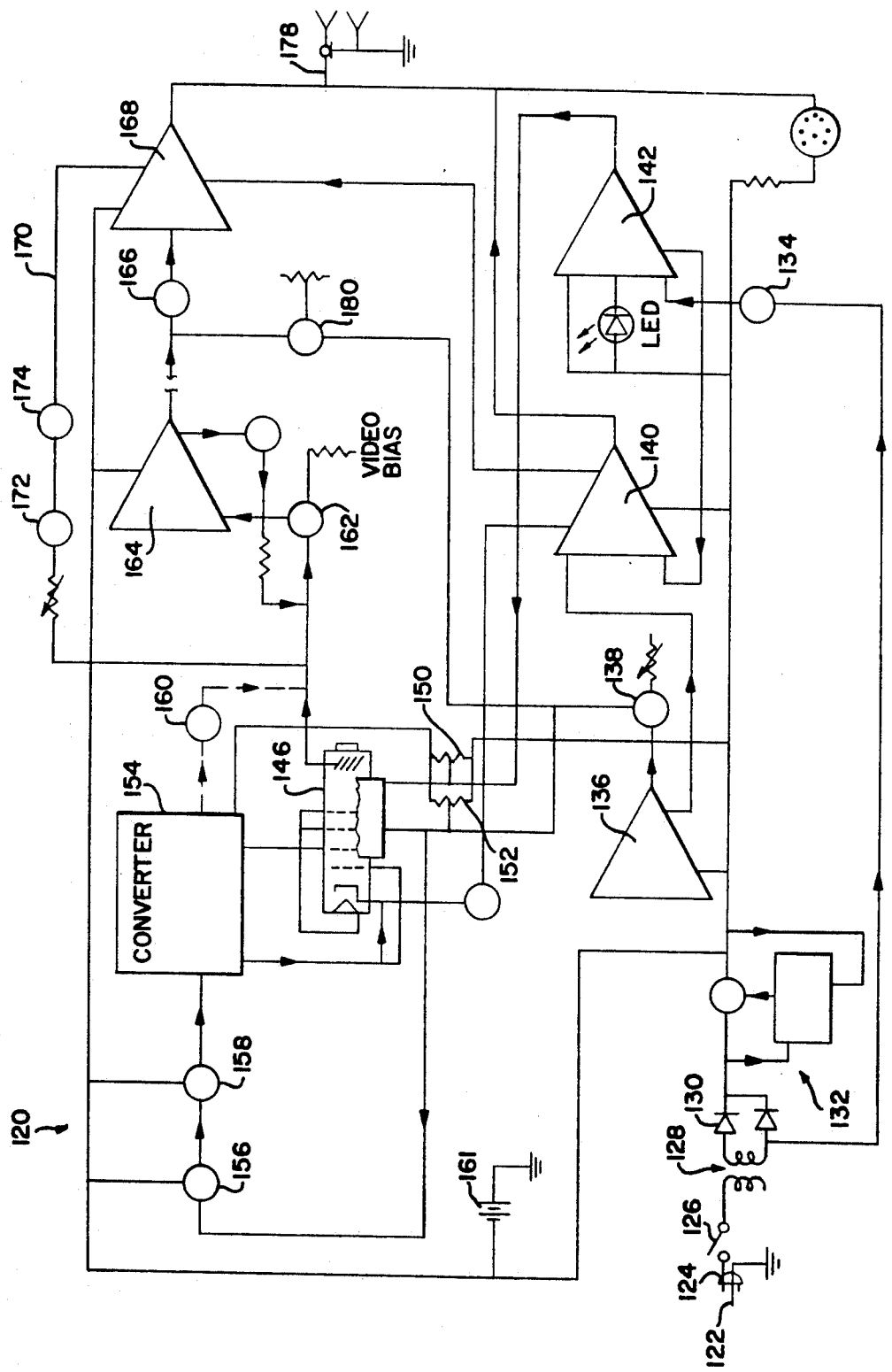

Having thus described the invention in general terms, reference will now be made to the accompanying drawings (five sheets) in which:

FIG. 1 is a side elevation view of a video camera and associated harness forming part of the video prothesis apparatus and shown on the head of a user;

FIG. 2 is a front elevational view of the video camera and harness of FIG. 1 on the head of an individual;

FIG. 3 is a top plan view of the video camera and harness arrangement;

FIG. 4 is a top plan view of the video camera with a top cover plate thereof removed;

FIG. 5 is a side elevational view of the video camera;

FIG. 6 is a front elevational view of a prothesis device for insertion into the eye cavity and which forms part of the video prothesis apparatus of the invention;

FIG. 7 is a side elevational view of the prothesis device of FIG. 6;

FIG. 8 is a side elevational view showing the connection of electrical conductors from the video camera to the prothesis device;

FIG. 9 is an end elevational view taken substantially along the plane of line 9—9 of FIG. 8;

FIG. 10 is a sectional view of a connector assembly forming part of the prothesis device;

FIG. 11 is a side elevational view showing the connecting plate assembly for connection of the electrical conductors to the optical nerve bundles;

FIG. 12 is an end elevational view taken substantially along the plane of line 12—12 of FIG. 11;

FIG. 13 is an end elevational view taken substantially along the plane of line 13—13 of FIG. 11;

FIG. 14 is a side elevational view, somewhat similar to FIG. 11, and showing an alternate arrangement for connecting the electrical conductors from the video camera to the optical nerve bundle;

FIG. 15 is an end elevational view taken substantially along the plane line 15—15 of FIG. 14; and FIG. 16 is a schematic circuit view showing a portion of the electrical circuitry forming part of the apparatus of the present invention.

DETAILED DESCRIPTION OF PREFERRED EMBODIMENTS

Referring now in more detail and by reference characters to the drawings, "A" designates a video prothesis apparatus comprising a video camera 20 suitably retained in a head harness 22. In this embodiment of the invention, the video camera is worn in a head harness and supported on the top of the head of the user. However, it should be understood that the video camera 20 could be supported in other forms.

The harness 22, in the embodiment as illustrated, comprises a strap 24 which extends around the wearer's head and a top strap 26 which extends over the crown of the wearer's head. A front plate 28 also forms a part of the harness. The plate 28, along with a box-like holding structure 30, form a frame for suitably receiving the video camera 20.

The video camera 20 contains a camera housing 32 along with a video camera unit 34 and a forwardly projecting lens 36. The focal length of the lens 36 is selected so as to simulate that of the normal human eye. The lens which is employed has a wider visual field than normal since it is not blocked by the nose as is the case in a person with normal sight. Accordingly, a greater peripheral view can result.

Mounted on the camera housing 30 and connected to the camera unit 32 is an off/on switch 38, an auto focus control 40 and a zoom lens control 42. Also located within the camera housing 30 is a microprocessor 44 and a reducing circuit 46 both of which are hereinafter described in more detail. However, it can be observed that the microprocessor 44 and the reducing circuit 46 (which may form part of the electrical circuitry 120, hereinafter described); are connected to the camera unit 34 through a cable 48.

The microprocessor 44 and the reducing circuit 46 are commonly found in video cameras of the type used herein with the visual prothesis apparatus.

The camera housing 30 is suitably mounted on the harness 22 through a pair of hinges 50. In this way, it is possible to adjust the physical angle of the camera housing 20 with respect to the harness and hence, with respect to the plane of the eyes of the user. In addition, an adjustment knob 52 is located at the rear portion of the camera housing for adjusting the angle of the housing with respect to the harness.

Inasmuch as the eye of the human being can move substantially within the eye socket so as to observe peripheral images and upper and lower images, it is desirable to simulate this as much as possible. Since the camera unit cannot move automatically, except with movement of the users head, the user can nevertheless cause the angle of the camera lens to change by adjustment of the knob 52.

The upper surface of the camera is provided with a solar panel 54 for providing electrical power to the electrically operable components of the eye prothesis apparatus as for example, the microprocessor, the reducing circuit and the camera unit. In addition, the housing 30 may be provided with storage batteries 56. In this case, the solar panels could be used to generate electrical power for recharging the batteries 56.

The camera housing 30 may also be provided with a removable cover plate (not shown) enabling access to the interior thereof if required. In this case, the top plate of the housing may be removably secured by means of screws 58 or like mechanical fasteners.

In the embodiment of the invention as illustrated in FIGS. 1-3, the prothesis apparatus is shown on the head of a user who is also wearing glasses or sunglasses. In some cases, this may be desirable in order to hide or to render somewhat inconspicuous, the conductor cable from the camera unit 34 to a prothesis device in the eye socket of an individual as hereinafter described.

The actual prothesis device forming part of the prothesis apparatus is more fully illustrated in FIGS. 6-13 of the drawings. The prothesis device 60 is in the shape of a spherical member having a size approximately equivalent to that of the eyeball so as to fit within the eye cavity when the damaged or injured eye has been removed. The spherical member 60 is generally of a two piece construction and is split along a centerline 61 to form device sections 60a and 60b. When the two sections 60a and 60b are secured together by screws 63, they form a semi-spherical internal chamber 62 which houses a connector assembly 64, the latter of which is hereinafter described in more detail. The spherical member 60 also includes a duct 66 which leads to and communicates with the internal chamber 62 and also communicates externally of the member 60 on a relatively flat exteriorly presented face 68.

The camera housing 20 is provided with a forwardly facing socket 70 which has a electrical connection with the microprocessor 44. A plug 72 is fitted within the socket 70 and has a current carrying conductor 74 for connection to the eye prothesis device. In this case, the other end of the cable 74 is connected directly to a so-called female connector 76 and which, is, in turn, adapted for connection to a male connector 78. The cable 74 is actually a cable carrying a plurality of individual electrical conductors. In this case, there is at least one conductor for each nerve in the optical nerve bundle extending from the brain to the eye socket.

The video camera 20 is designed to generate electrical signals, which in the composite, are capable of regenerating an image observed through the lens 36 of the video camera. Thus, when all of the structural signals are used to generate visual images in the proper sequence, they can re-create the original image which is detected by the lens 36 These individual signals are carried by the individual electrical conductors in the cable 74 and to the eye prothesis device 60.

FIGS. 8 and 9 more fully illustrate the arrangement of the male connector 72 and the female connector 76 and the connector 78. In this case, it can be observed that the male connector 72 includes a key 80 for proper orientation and alignment of the connector 72 in the socket 70. The key 80 is adapted to fit only one orientation in a key way in the socket 70. In like manner, the plug 76 is provided with a key 83 also fitting within the key way 82 in order to maintain proper orientation. Finally, the connector 78 is provided with a key 84 also fitting within the key way 82.

By reference to FIG. 9, it can be observed that the male connector 78 is generally circular in cross section and includes the individual electrical conductors 86 contained within the cable 74.

The individual conductors in the male connector 78 are connected to the connector assembly 64, as best illustrated in FIG. 10 of the drawings. In this case, the connector assembly 64 comprises a pair of plates 90 and 92. Extending between the plates 90 and 92 are electrical contact pins 94. In this case, it can be observed that the individual conductors 86 are connected to the individual contact pins 94. In this case, there will be a separate contact pin 94 for each conductor 86.

The plate 92 also receives the electrical contact pins 94 in the manner as best illustrated in FIGS. 10-13 of the drawings. Further, each one of the individual optical nerves 96 are also connected to the electrical contact pins 94 in a manner to be hereinafter described in more detail. However, when the optical nerves are so connected, it can be observed that a separate electrical signal carried on each conductor is transmitted to a separate one of the optical nerves 96 so that an image observed by the video camera can be re-generated in the brain of the individual.

By reference to FIGS. 12 and 13, it can be observed that the individual optical nerves 96 are arranged in a circular array. In like manner, the individual electrical conductors 86 are arranged in a circular array. It should be understood that the optical nerves 96 could be arranged in a somewhat rectangular pattern if the plate 92 adopts a form of a rectangularly shaped plate 100 in the nature of a carding plate. In like manner, the carding plate 100 would operate with a similar carding plate 102 and which are respectively substantially similar to the plates 92 and 90, respectively.

The optical prothesis device 60 is provided with a safety clip 106 to removably hold the connector 76 in the prothesis device 60. The device 60 is also provided with a moisture seal 107 between the housing sections 60a and 60b along with an end seal 108 as best shown in FIGS. 6 and 7. In this way, the electrical conductors can enter into the duct 66, but moisture and other impurities are precluded from entering this duct and which impurities or dust would otherwise affect the optical nerves.

The eye prothesis device 60 is a precision made device. The holes for the conductors and the key slot and the keys are precisely made so that there is a precise alignment of the wires which carry the nerve impulses through the system. The individual conductors 86 may be connected to the various contact pins 94 by means of glue or other conventional means known in the art. However, the pins could be pulled in and out of the holes in which they are fitted in the event that it is necessary to disassemble the device. The optical nerves 96 would obviously be implanted by and connected to the pins by a microsurgeon and held in place with Millipore porous paper material which will enable a tight adherence of the nerves to the contact pin.

The prothesis apparatus of the present invention employs a special circuit 120 which is more fully illustrated in FIG. 16 of the drawings. This circuit 120 is somewhat similar to closed loop circuits of the type used in some video recording and reproducing equipment. The circuit is more fully illustrated in its schematic form in FIG. 16. The circuit generally receives an input 122 from the video camera at an and gate 124. The and gate 124 is provided with one grounded output and another output connected directly to an off-on switch 126. When the switch 126 is open, the camera effectively will not operate. This switch 126 may be coupled to or it may be the same as the switch 36.

The input signal is introduced into a step-up transformer 128 and both of the terminals of which are connected through diodes 130 to a regulator circuit 132. This regulator circuit 132 is generally of a conventional arrangement and is designed to provide current and voltage regulation to the signal. One of the outputs of the secondary of the transformer 128 is connected directly to a zero cross detector 134 and which is hereinafter described in more detail.

The regulator 132 provides a positive voltage signal which is effectively designed to operate the remaining portion of the circuit. For this purpose, the regulator may be provided with or connected to a suitable power supply (not shown). The output of the regulator 132 is introduced into a horizontal oscillator 136 and which has an output introduced directly into a horizontal driver 138. The oscillator 136 also has an input to a blank mixer 140 and which, in turn, receives a feedback input from a vertical oscillator 142. The oscillator 142 further receives an input directly from the secondary of the transformer 128 and an input from the zero cross detector 134.

The oscillator output effectively operates as a deflection signal and this is introduced into a yoke 146 which similarly receives a signal from the horizontal driver 138. Potentiometer 150 and 152 in the circuit of the respective signals from the oscillator 142 and the horizontal driver 138 serve, respectively, as a vertical centering adjustment and as a horizontal centering adjustment. These two potentiometers 150 and 152 are thereupon designed to center the video image at the camera. Further, these adjustments are internal and are only employed in setting up the prothesis apparatus.

The yoke 146 also receives an input from a direct current converter 154. The yoke 146 has an output directly to a current amplifier 156 which is, in turn, connected to a current driver 158 and the output of this current driver 158 is introduced into the D.C. converter 154. An additional current amplifier 160 can optionally be employed, if required. For this reason, the amplifier 160 is shown only as being connected in dotted lines. The entire circuit is operable from a battery source of power 161. In this case a conventional 6 volt or 12 volt battery source of power would be provided. An additional power regulator could be provided if required.

The yoke 146 further has an output connected to a cascading amplifier 162 and which has a grounded bias potentiometer connected thereto as shown in FIG. 16. The cascading amplifier receives an output from and has an input directed into a high peak gain video preamplifier 164. The output of the video preamplifier is introduced through an amplifier 166 and into a video processing clipper 168. It can be observed that this clipper 168 receives a peak average signal 170 from the yoke and which passes through setting amplifiers 172 and 174. The output of the video processing clipper 168 is combined with the output of the mixer 140 and provides a video output signal 178. In some cases, a pedestal clamp 180 may be employed as shown in FIG. 16.

In the actual use of the prothesis apparatus, the prothesis device is inserted into the eye cavity as previously described. The prothesis device which effectively replaces the human eye will send electrical signals representing a visual image through the optical nerve system directly to the brain.

Each optical nerve has a diameter of about 1.1 millimeter, that is, starting from a child of about age 8 through the remainder of life. Thus, a large number of the optical nerves and pins can be fitted within a relatively small space.

It is necessary to ensure that all of the optical nerves are correctly matched with the individual conductors 86, that is, to ensure that each conductor 86 is connected to the proper optical nerve. Matching of the optical nerve to the individual conductors may be accomplished with the aid of a computer. Thus, when each individual optical nerve is connected to an electrical conductor through the connector assembly previously described, the microsurgeon will inquire if the individual has detected a spot of light. If there is no spot of light detected by the individual, then there is an improper match of the optical nerve to the individual contact pin. In like manner, if there is a spot of light observed, then that combination which may represent a correct combination is noted.

After the correct combinations have been established, enhancement, refinement focusing and reducing or boosting the current to a safe range will occur until the sight has been optimized. The process of connecting the optical nerves to the individual contact pins is essentially a trial and error process with each correct combination being noted. Thus, when all combinations have been determined, the individual optical nerves can be connected to the appropriate contact pins.

In accordance with the arrangement as set forth herein, when an image is observed by the video camera, the electrical signals of that image are generated by the camera and transmitted to the eye prothesis device, as previously described. These electrical signals are thereupon carried to the cortex of the brain where they are then reconverted into the original image, much in the same manner as with the normal visual process.

The electrical signals are obviously low voltage electrical signals and the current levels are those which are adapted to match the current levels normally present in the electrical signals processed by the brain. Thus, and in this case, it is intended to match the actual visual process as closely as possible. The electrical signals which are transmitted from the video camera are again conditioned to approximate those electrical signals which would be transmitted over the optical nerves in a normal sight operation.

Thus, there has been illustrated and described a unique and novel prothesis apparatus which aids in the sight of an individual having a diseased or injured eye and in which sight has been impaired or eliminated. The prothesis device and the method of the present invention therefore fulfill all of the objects and advantages which have been sought. It should be understood that many changes, modifications, variations and other uses and applications will become apparent to those skilled in the art after considering the specification and the accompanying drawings. Therefore, any and all such changes, modifications, variations and other uses and applications which do not depart from the spirit and scope of the invention are deemed to be covered by the invention.

Having thus described the invention, what I desire to claim and secure by letters patent is:

1. A visual prothesis apparatus for operative insertion in the optical pathway to the brain of an individual having an eye which is blind or partially blind, said apparatus comprising:
   a) a video camera having means for generating a plurality of individual video signals in response to viewing of an image over a period of time,
   b) an insert for implantation in the eye socket in place of the eye which is blind or partially blind,
   c) connecting means in said insert enabling receipt of video signals from the video camera and having a number of individual terminals so that each terminal will carry a separate one of the video signals, d) cable means for electrically connecting the video camera to the connecting means in said insert and for delivering the video signals to the insert, the cable means carrying the individual video signals generated by said video camera to the individual terminals of said connecting means, e) an optical nerve connecting assembly in said insert and having a plurality of individual nerve connecting terminals connected to said terminals of said connecting means such that each individual terminals of the connecting means receives a separate one of the video signals, and said nerve connecting assembly having communication means for causing electrical communication between each terminal and an optical nerve of the individual so that each optical nerve can receive the separate video signal associated with that optical nerve.

2. The visual prothesis apparatus of claim 1 further characterized in that said cable means comprises:

a) a first connector for connection to a video signal outlet on said video camera, and b) a second connector for connection to a mating video signal adapter in said insert and for delivering video signals generated by said camera thereto.

3. The visual prothesis apparatus of claim 2 further characterized in that said optical nerve connecting assembly comprises:

a) a first plate having a plurality of contact pins with each for connection to a separate and individual conductor of said cable means, b) a second plate having a plurality of openings with each to receive a separate one of the optical nerves, c) said first and second plates being arranged so that each contact pin can be connected to a separate one of the individual optical nerves and where the signals received at each contact pin in combination represent the image viewed by the video camera, and d) whereby each optical nerve receives a separate signal representative of a portion of the viewed image and where all of the signals from each of the conductors will in combination and proper orientation represent a complete visual image.

4. The visual prothesis apparatus of claim 3 further characterized in that the first and second plates of said optical nerve connecting assembly are abutted against one another so that each of the nerves in said openings come into contact with the contact pins.

5. The visual prothesis apparatus of claim 2 further characterized in that said insert comprises an interior chamber which holds said optical nerve connecting assembly and said adapter extends into said chamber.

6. The visual prothesis apparatus of claim 1 further characterized in that said apparatus comprises a harness means capable of being worn on a head of a user of the apparatus and the harness means carries the video camera.

7. A visual prothesis device for insertion in the eye socket of an individual in place of an eye which is blind or partially blind, said prothesis device comprises:

a) connector means for receiving a plurality of video signals of an image on separate conductors and where all of the video signals in combination represent the image, b) a housing having an interior cavity therein, c) an adapter connected to connector means and said adapter extending and being comprised of:

1) a first plate having a plurality of contact pins with each for connection to a separate and individual conductor to said connecting means, 2) a second plate having a plurality of openings with each to receive a separate one of the optical nerves, and 3) said first and second plates being arranged so that each contact pin can be connected to a separate one of the individual optical nerves and whereby each optical nerve receives a signal representative of a portion of the viewed image and where all of the signals from each of the conductors represent a complete visual image.

8. The visual prothesis device of claim 7 further characterized in that the first and second plates of said optical nerve connecting assembly are abutted so that ends of the nerves in said openings come into contact with the contact pins.

9. The visual prothesis device of claim 7 further characterized in that said device is representative of an eye which it replaces.

10. The visual prothesis device of claim 9 further characterized in that said cavity is hermetically sealed with respect to the external atmosphere.

11. A process for improving the sight of an individual having an eye which is blind or partially blind by use of a prothesis apparatus operatively inserted in the optical pathway to the brain of the individual, said process comprising:

a) generating a plurality of individual video signals by a video camera in response to viewing of an image and where each of the video signals in combination represent a composite of the image viewed over a selected period of time, b) removing an eye which is blind or partially blind from an eye socket and inserting a prothesis device into the eye socket, c) connecting a cable from the video camera to the prothesis device and which cable contains a separate conductor for each video signal to enable receipt of video signals from the video camera and each conductor having a terminal with each carrying a separate one of the individual video signals, d) determining the correct combination of each conductor and each optical nerve so that the conductors carrying a signal representation of the viewed image are connected to the proper nerves so that all signals in proper orientation will recreate the visual image, and e) connecting the terminal of each conductor to a separate one of the optical nerves so that each optical nerve is connected to a separate conductor and each optical nerve receiving a separate video signal associated with that optical nerve, so that all of the video signals in combination can be used to recreate the visual image.

12. The process of claim 11 further characterized in that the number of conductors is approximately equal to the number of nerves.

13. The process of claim 11 further characterized in that the process comprises connecting the terminal of each said conductor through a separate one of a plurality of terminal pins to a separate one of the optical nerves.

14. In a visual prothesis apparatus having a prothesis device which is provided for operative insertion into the eye socket of an individual in the optical pathway to the brain of the individual having an eye which is blind or partially blind, said prothesis device receiving a plurality of electrical signals from a video camera forming part of said apparatus in response to viewing an image and which signals are connected through a connecting means associated with said prothesis device to an optical nerve so that each optical nerve receives a separate electrical signal and where each of the electrical circuit for processing the electrical signals into a form where they can be combined to represent the composite of the viewed image, said electrical circuit comprising:
 a) a converter for receiving each signal and converting each said signal to an equivalent D.C. signal,
 b) a video amplification section receiving the converted D.C. signal for increasing the peak gain of the converted D.C. signal to provide a peak average signal,
 c) a horizontal and vertical centering circuit arrangement connected to said video amplification section for centering an image which is to be generated by the video camera, and
 d) video processing clipping means receiving the peak average signals of the video amplification section and processing the amplified signals for generating an output signal.

15. The electrical circuit for use with the prothesis apparatus of claim 14 further characterized in that said horizontal and vertical centering circuit arrangement comprises a separate horizontal centering circuit and a separate vertical centering circuit arrangement.

16. The electrical circuit for use with the prothesis apparatus of claim 14 further characterized in that a horizontal driver is operatively coupled to an output from the video pre-amplifier.

17. The electrical circuit for use with the prothesis apparatus of claim 14 further characterized in that a blank mixer provides an input to the clipping video processing means.

18. A visual prothesis device for insertion in the eye socket of an individual in place of an eye which is blind or partially blind, said prothesis device comprises:
 a) connector means for receiving a plurality of video signals of an image on separate conductors and where all of the video signals in combination represent the image,
 b) a housing having an interior cavity therein, said housing having a size and shape similar to that of an eye which it is to replace so as to represent that eye,
 c) an adapter with said housing connected to connector means and said adapter extending into said interior cavity,
 d) an optical nerve connecting assembly in said interior cavity and being comprised of:
  1) a first plate having a plurality of contact pins with each for connection to a separate and individual conductor to said connecting means,
  2) a second plate having a plurality of openings with each to receive a separate one of the optical nerves, and
  3) said first and second plates being arranged so that each contact pin can be connected to a separate one of the individual optical nerves and whereby each optical nerve receives a signal representative of a portion of the viewed image and where all of the signals from each of the conductors represent a complete visual image.

19. The visual prothesis device of claim 18 further characterized in that said cavity is hermetically sealed with respect to the external atmosphere.

* * * * *